(12) United States Patent
Kimura

(10) Patent No.: US 10,033,955 B2
(45) Date of Patent: Jul. 24, 2018

(54) X-RAY DETECTOR AND X-RAY APPARATUS

(71) Applicant: Samsung Electronics Co., Ltd., Gyeonggi-do (KR)

(72) Inventor: Hisashi Kimura, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 15/508,452

(22) PCT Filed: Sep. 1, 2015

(86) PCT No.: PCT/KR2015/009188
§ 371 (c)(1),
(2) Date: Mar. 2, 2017

(87) PCT Pub. No.: WO2016/036108
PCT Pub. Date: Mar. 10, 2016

(65) Prior Publication Data
US 2017/0295336 A1 Oct. 12, 2017

(30) Foreign Application Priority Data
Sep. 2, 2014 (KR) .................. 10-2014-0116376

(51) Int. Cl.
*H01L 27/146* (2006.01)
*H04N 5/378* (2011.01)
(Continued)

(52) U.S. Cl.
CPC ............. *H04N 5/378* (2013.01); *A61B 6/548* (2013.01); *H04N 5/3745* (2013.01);
(Continued)

(58) Field of Classification Search
CPC ........ H04N 3/1568; H04N 5/32; H04N 5/357; H04N 5/3577; G01T 1/20
See application file for complete search history.

(56) References Cited

U.S. PATENT DOCUMENTS

2005/0218332 A1 10/2005 Rutten et al.
2009/0194672 A1 8/2009 Tredwell et al.
(Continued)

FOREIGN PATENT DOCUMENTS

JP 2014-071034 A 4/2014
KR 10-2012-0019741 A 3/2012

OTHER PUBLICATIONS

The International Searching Authority, "Notification of Transmittal of the International Search Report and the Written Opinion of the International Searching Authority, or the Declaration," International Application No. PCT/KR2015/009188, dated Dec. 10, 2015, 10 pages, publisher The ISA/KR, International Application Division, Korean Intellectual Property Office, Daejeon, Republic of Korea.

*Primary Examiner* — Kiho Kim

(57) ABSTRACT

An X-ray detector includes a plurality of photodiodes arranged in a matrix shape and respectively connected to switching devices, a plurality of gate lines formed in a first direction and connected to the switching devices; a plurality of data lines, wherein N data lines are formed in each second-direction column of the matrix shape, wherein N is greater than 1; and a read-out circuit connected to the plurality of data lines and configured to read out photocurrents from the plurality of photodiodes and convert the photocurrents into X-ray image data, wherein each of switching devices included in each second-direction column of the matrix shape is connected to one of the N data lines.

20 Claims, 8 Drawing Sheets

(51) Int. Cl.
  *H04N 5/3745* (2011.01)
  *A61B 6/00* (2006.01)
  *H04N 5/32* (2006.01)

(52) U.S. Cl.
  CPC ............ *A61B 6/4405* (2013.01); *A61B 6/542* (2013.01); *H04N 5/32* (2013.01)

(56) References Cited

U.S. PATENT DOCUMENTS

| | | |
|---|---|---|
| 2012/0138808 A1 | 6/2012 | Jung |
| 2012/0199750 A1* | 8/2012 | Kondou ................. H04N 5/32 250/370.09 |
| 2012/0219203 A1* | 8/2012 | Adachi ................. A61B 6/585 382/132 |
| 2012/0257439 A1 | 10/2012 | Kurokawa |
| 2015/0192684 A1 | 7/2015 | Ito |

* cited by examiner

[Fig. 1]
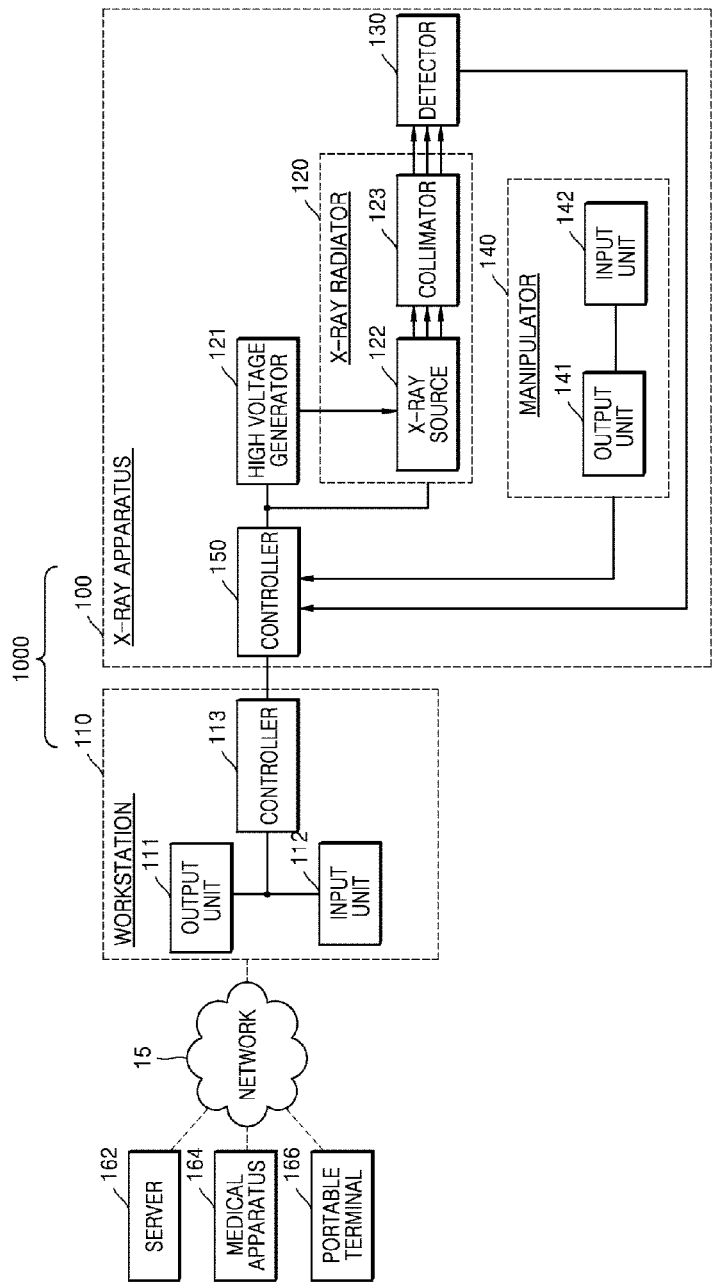

[Fig. 2]
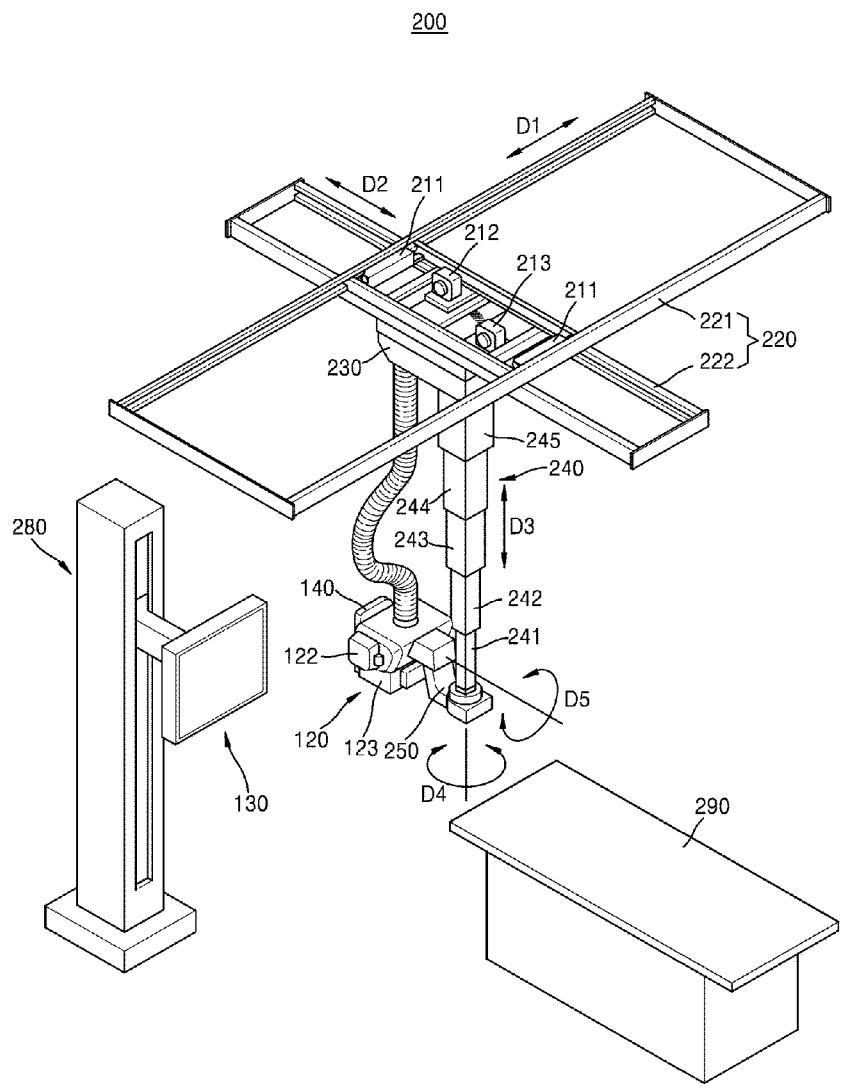

[Fig. 3]
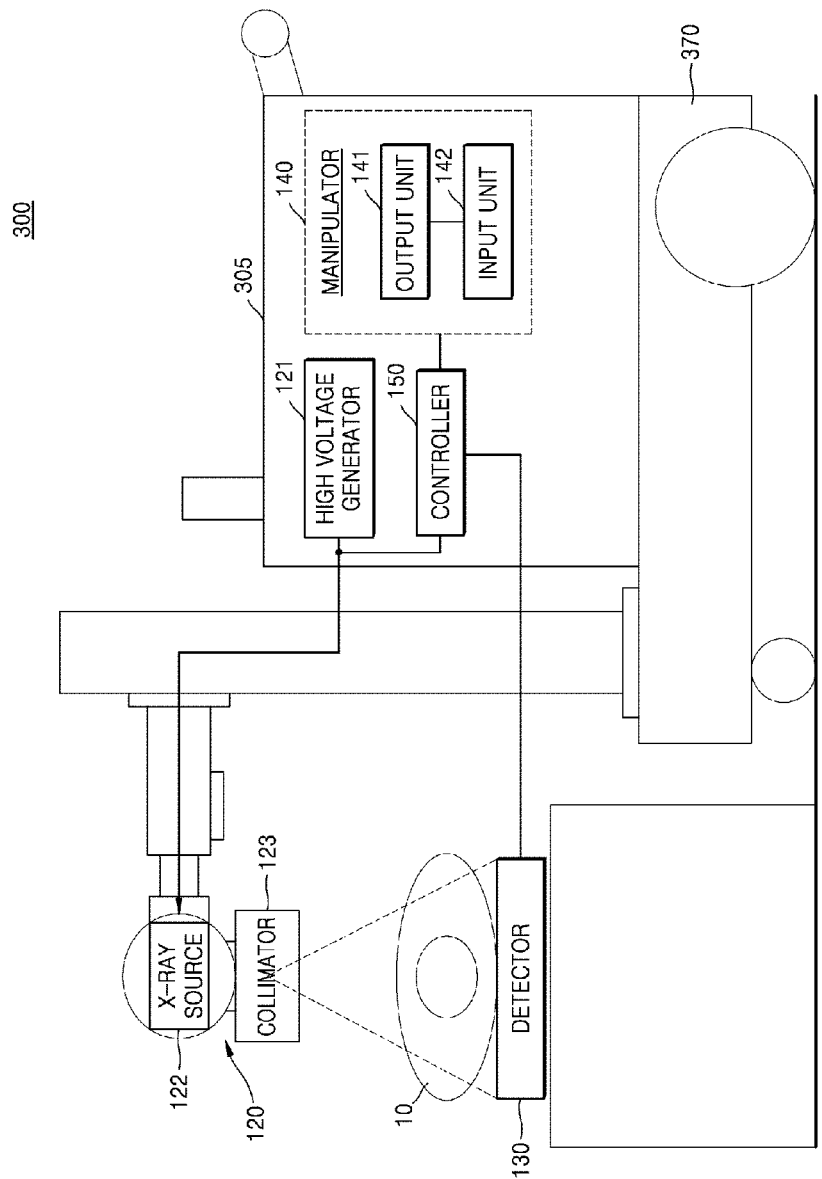

[Fig. 4]
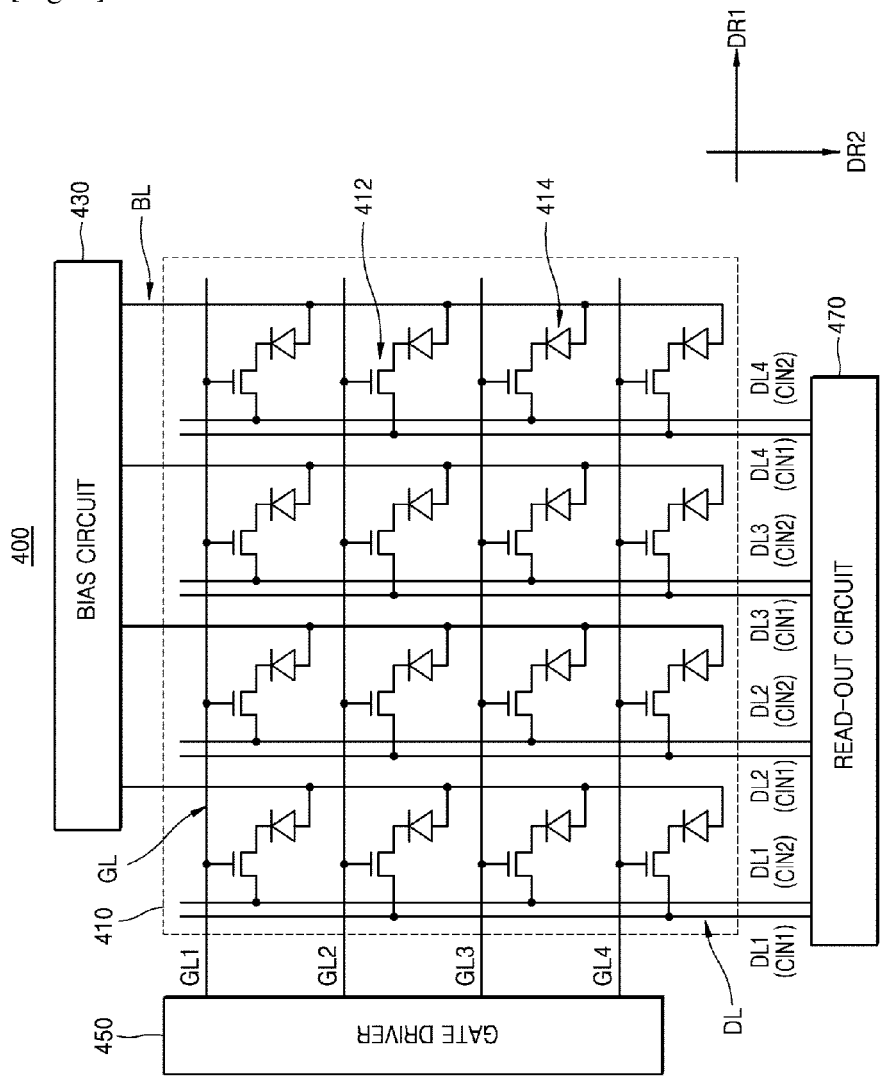
[Fig. 5]
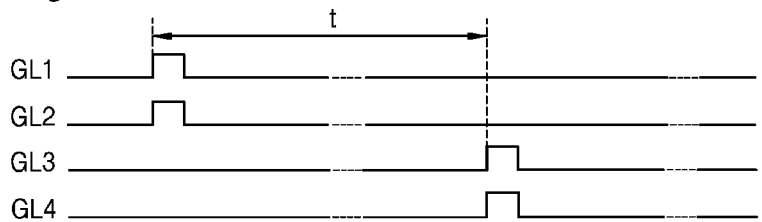

[Fig. 6]
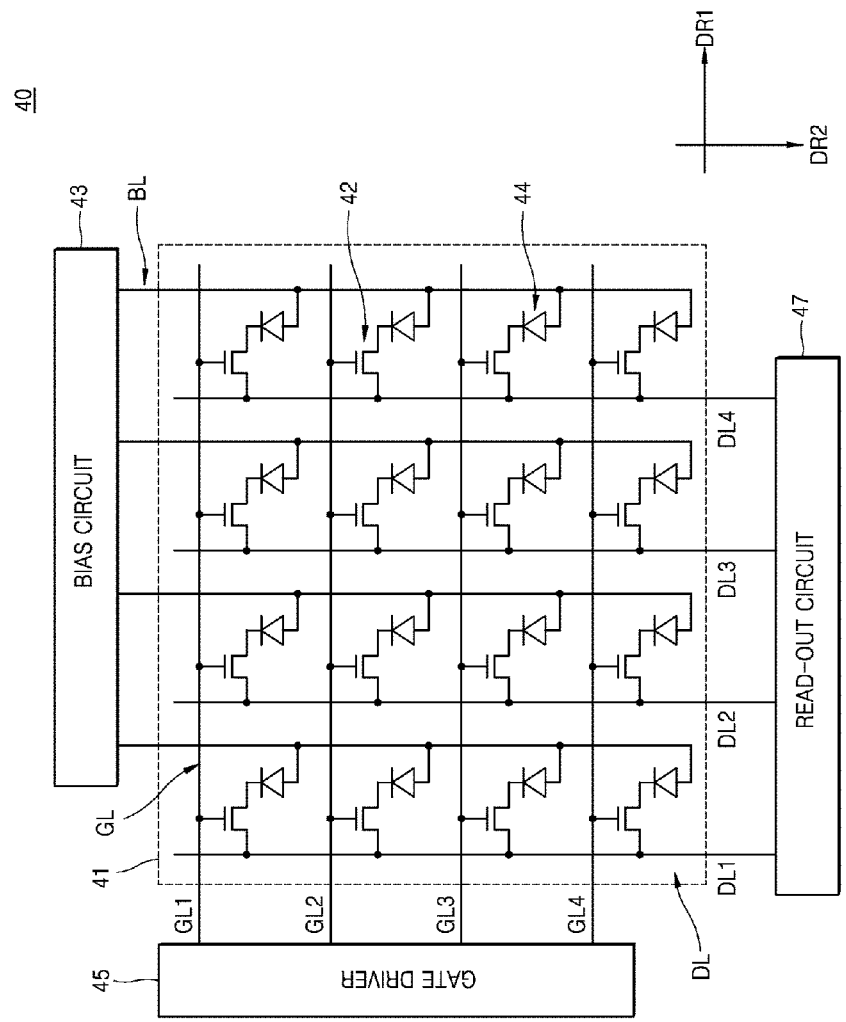

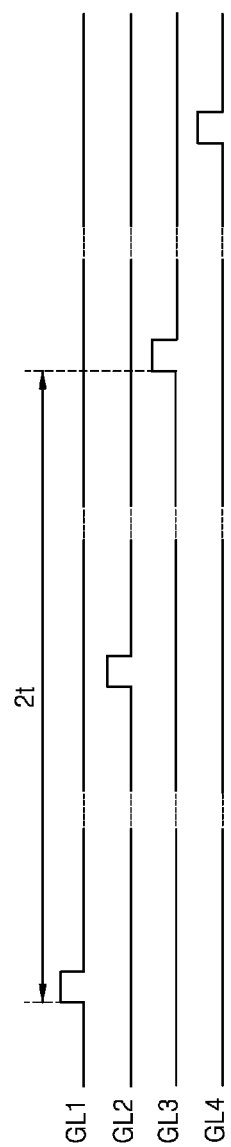

[Fig. 8]
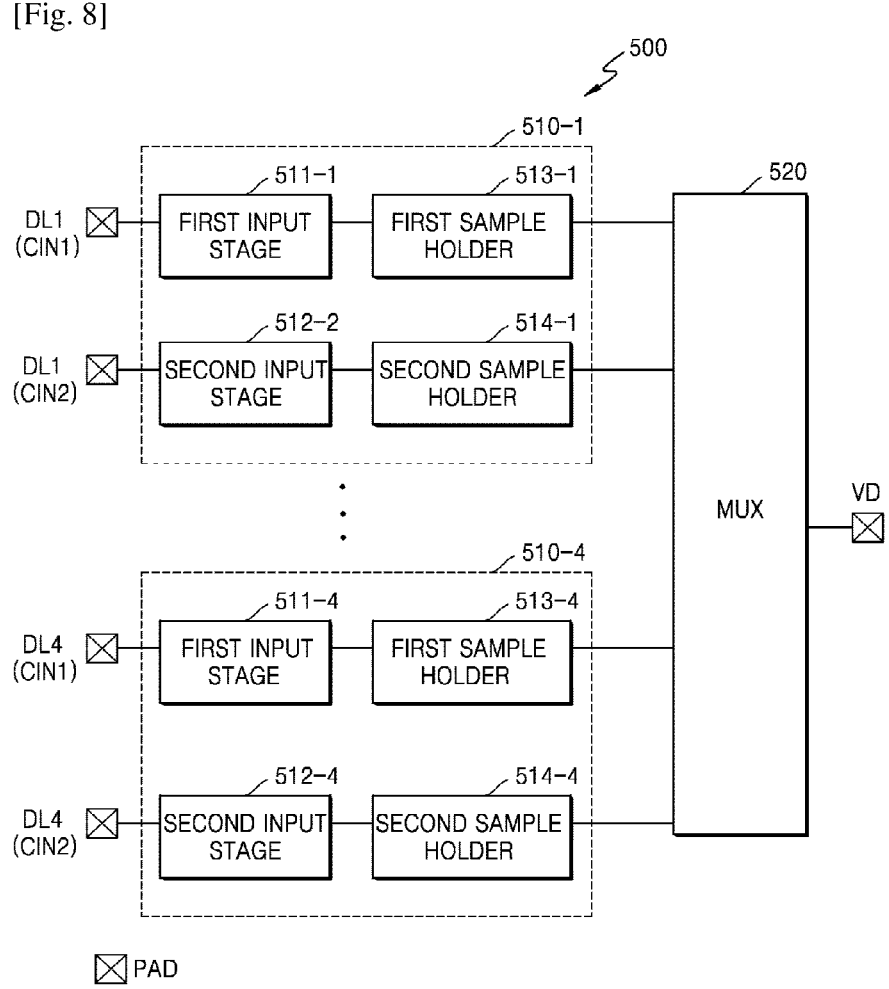

[Fig. 9]
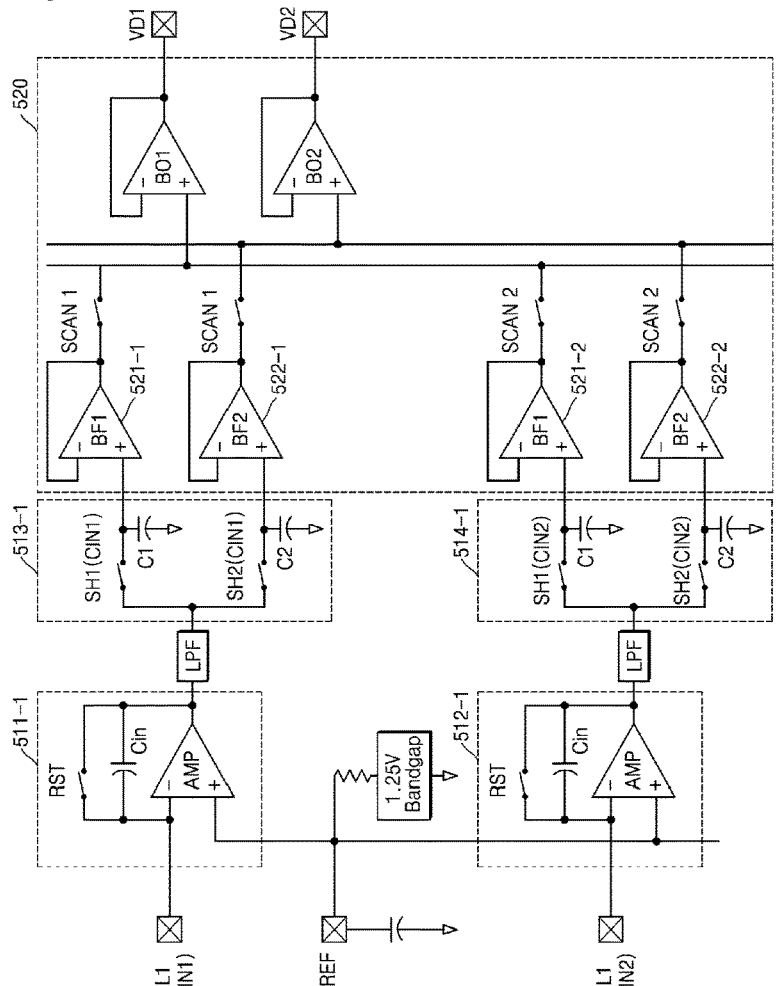
[Fig. 10]
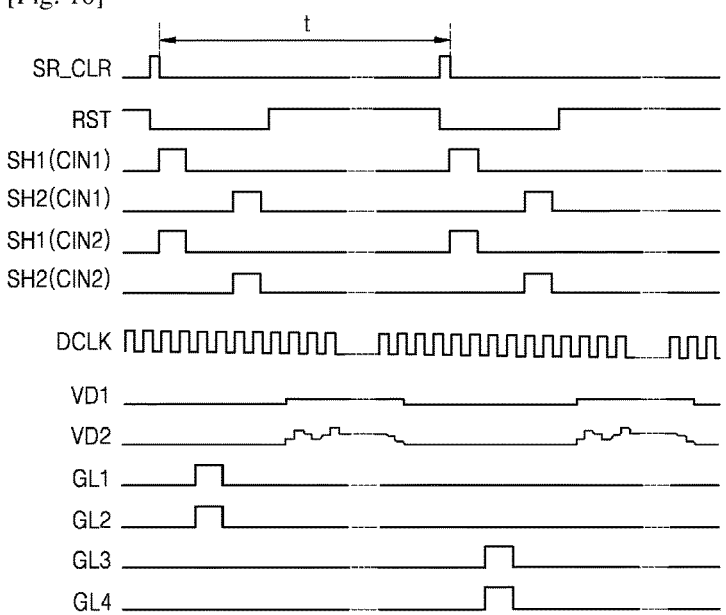

X-RAY DETECTOR AND X-RAY APPARATUS

TECHNICAL FIELD

One or more exemplary embodiments relate to an X-ray detector and an X-ray apparatus, and more particularly, to an X-ray detector and an X-ray apparatus whereby the X-ray detection speed is improved.

BACKGROUND ART

X-rays are electromagnetic waves having a wavelength of about 0.01 Å to 100 Å. Since X-rays can pass through many materials, X-rays are widely used in medical devices for photographing inner organs of living bodies or industrial nondestructive inspection devices.

X-ray apparatuses may take X-ray images of an object by irradiating the object with X-rays emitted from an X-ray source and detecting the intensity difference between X-rays passing through the object using an X-ray detector. The inside structure of the object may be checked using the X-ray images, and then the object may be diagnosed. The inside structures of objects may easily be checked using X-ray apparatuses that operate on the principle that the transmittance of X-rays varies according to the densities of the objects and the atomic numbers of atoms constituting the objects. Short-wavelength X-rays have high transmittance and thus provide bright images.

DISCLOSURE

Technical Solution

According to one or more exemplary embodiments, an X-ray detector includes: a plurality of photodiodes arranged in a matrix shape and respectively connected to switching devices; a plurality of gate lines formed in a first direction and connected to the switching devices; a plurality of data lines, wherein N data lines are formed in each second-direction column of the matrix shape wherein N is greater than 1; and a read-out circuit connected to the plurality of data lines and configured to read out photocurrents from the plurality of photodiodes and convert the photocurrents into X-ray image data, wherein each of switching devices included in each second-direction column of the matrix shape is connected to one of the N data lines.

Advantageous Effects

One or more exemplary embodiments include an X-ray detector and an X-ray apparatus whereby the X-ray detection speed is improved.

DESCRIPTION OF DRAWINGS

These and/or other aspects will become apparent and more readily appreciated from the following description of the exemplary embodiments, taken in conjunction with the accompanying drawings in which:

FIG. 1 is a block diagram of an X-ray system;
FIG. 2 is a perspective view of a fixed type X-ray apparatus;
FIG. 3 is a view of a mobile X-ray apparatus;
FIG. 4 is a view illustrating an X-ray detector according to an exemplary embodiment;
FIG. 5 is a view illustrating exemplary waveforms of gate signals applied from a gate driver of the X-ray detector illustrated in FIG. 4;
FIG. 6 is a view of an X-ray detector provided not in accordance with the exemplary embodiment;
FIG. 7 is a view illustrating exemplary waveforms of gate signals applied from a gate driver of the X-ray detector illustrated in FIG. 6;
FIG. 8 is a view illustrating a read-out circuit included in the X-ray detector of the exemplary embodiment;
FIG. 9 is a view illustrating examples of a sample holder unit and a multiplexer of the read-out circuit illustrated in FIG. 8; and
FIG. 10 is a view illustrating exemplary waveforms of signals applied to elements of the X-ray detector illustrated in FIGS. 4 and 9.

BEST MODE

According to one or more exemplary embodiments, an X-ray detector includes: a plurality of photodiodes arranged in a matrix shape and respectively connected to switching devices; a plurality of gate lines formed in a first direction and connected to the switching devices; a plurality of data lines, wherein N data lines are formed in each second-direction column of the matrix shape wherein N is greater than 1; and a read-out circuit connected to the plurality of data lines and configured to read out photocurrents from the plurality of photodiodes and convert the photocurrents into X-ray image data, wherein each of switching devices included in each second-direction column of the matrix shape is connected to one of the N data lines.

The X-ray detector may further include a gate driver connected to the plurality of gate lines and configured to apply turn-on signals for turning on the switching devices, wherein the gate signals may be simultaneously applied to N switching devices of the switching devices included in each second-direction column and connected to different data lines.

Switching devices included in N rows formed in the first direction in the matrix shape may be simultaneously turned on by the gate signals.

Photocurrents from photodiodes connected to the turned-on switching devices may be input to the read-out circuit through data lines connected to the turned-on switching devices.

The read-out circuit may include: N sample holders connected to the N data lines formed in each second-direction column of the matrix shape; and a multiplexer connected to the N sample holders.

The N sample holders may be configured to accumulate sample electric charges based on photocurrents from photodiodes that are electrically respectively connected to the N sample holders, and the multiplexer may be configured to sequentially output the sample electric charges accumulated in the N sample holders.

The read-out circuit further may include input stages between the data lines and the sample holders, wherein the input stages may include input capacitors configured to accumulate photocharges based on the photocurrents.

Each of the N sample holders may include a first capacitor and a second capacitor, wherein, before the switching devices included in the N rows are simultaneously turned on by the gate signals, the first capacitors may electrically connected to the input capacitors and accumulate first sample electric charges, and after the switching devices included in the N rows are simultaneously turned on by the gate signals, the second capacitors may electrically connected to the input capacitors and accumulate second sample electric charges based on the photocharges.

The multiplexer may be configured to simultaneously output the first and second sample electric charges.

The read-out circuit may be configured to obtain the X-ray image data based on a difference between the first and second sample electric charges.

According to one or more exemplary embodiments, an X-ray apparatus includes: an X-ray radiator configured to radiate X-rays; and a detector configured to detect the radiated X-rays, wherein the detector includes: a scintillator converting the X-rays into light; a plurality of photodiodes arranged in a matrix shape and respectively connected to switching devices; a plurality of gate lines formed in a first direction and connected to the switching devices; a plurality of data lines, wherein N data lines are formed in each second-direction column of the matrix shape wherein N is greater than 1; and a read-out circuit connected to the plurality of data lines and configured to read out photocurrents from the plurality of photodiodes and convert the photocurrents into X-ray image data, wherein each of switching devices included in each second-direction column of the matrix shape is connected to one of the N data lines.

The detector may further include a gate driver connected to the plurality of gate lines and configured to apply turn-on signals to turn on the switching devices, wherein the gate signals may be simultaneously applied to N switching devices of the switching devices included in each second-direction column and connected to different data lines.

MODE FOR INVENTION

This application claims the benefit of Korean Patent Application No. 10-2014-0116376, filed on Sep. 2, 2014, in the Korean Intellectual Property Office, the disclosure of which is incorporated herein in its entirety by reference.

Additional aspects will be set forth in part in the description which follows and, in part, will be apparent from the description, or may be learned by practice of the presented exemplary embodiments.

The attached drawings for illustrating exemplary embodiments of the present disclosure are referred to in order to gain a sufficient understanding of the present disclosure, the merits thereof, and the objectives accomplished by the implementation of the present disclosure. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present disclosure will only be defined by the appended claims.

Hereinafter, the terms used in the specification will be briefly described, and then the present disclosure will be described in detail.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the present disclosure.

Throughout the specification, an "image" may denote multi-dimensional data composed of discrete image elements (for example, pixels in a two-dimensional image and voxels in a three-dimensional image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

In addition, an "object" may be a human, an animal, or a part of a human or animal. For example, the object may include an organ (for example, the liver, the heart, the womb, the brain, breasts, or the abdomen), blood vessels, or a combination thereof. The object may be a phantom. The phantom denotes a material having a volume, a density, and an effective atomic number that are approximately the same as those of a living organism. For example, the phantom may be a spherical phantom having similar properties to those of the human body.

Throughout the specification, a "user" may be, but is not limited to, a medical expert, for example, a medical doctor, a nurse, a medical laboratory technologist, or a medical imaging expert, or a technician who repairs medical apparatuses.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest photographing, simple abdomen photographing, simple skeleton photographing, simple nasal sinuses photographing, simple neck soft tissue photographing, and breast photographing.

FIG. 1 is a block diagram of an X-ray system 1000.

Referring to FIG. 1, the X-ray system 1000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray radiator 120, a high voltage generator 121, a detector 130, a manipulator 140, and a controller 150. The controller 150 may control overall operations of the X-ray apparatus 100.

The high voltage generator 121 generates a high voltage for generating X-rays, and applies the high voltage to an X-ray source 122.

The X-ray radiator 120 includes the X-ray source 122 receiving the high voltage from the high voltage generator 121 to generate and radiate X-rays, and a collimator 123 for guiding a path of the X-ray radiated from the X-ray source 122 and adjusting an irradiation region radiated by the X-ray.

The X-ray source 122 includes an X-ray tube that may be realized as a vacuum tube diode including a cathode and an anode. An inside of the X-ray tube is set as a high vacuum state of about 10 mmHg, and a filament of the anode is heated to a high temperature to generate thermal electrons. The filament may be a tungsten filament, and a voltage of about 10V and a current of about 3 to 5 A may be applied to an electric wire connected to the filament to heat the filament.

In addition, when a high voltage of about 10 to about 300 kVp is applied between the cathode and the anode, the thermal electrons are accelerated to collide with a target material of the cathode, and then, an X-ray is generated. The X-ray is radiated outside via a window, and the window may be formed of a beryllium thin film. In this case, most of the energy of the electrons colliding with the target material is consumed as heat, and remaining energy is converted into the X-ray.

The cathode is mainly formed of copper, and the target material is disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, an energy of the X-ray (energy of photon) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detector 130 detects an X-ray that is radiated from the X-ray radiator 120 and has been transmitted through an object. The detector 130 may be a digital detector. The detector 130 may be implemented by using a thin film transistor (TFT) or a charge coupled device (CCD). Although the detector 130 is included in the X-ray apparatus 100 in FIG. 1, the detector 130 may be an X-ray detector that is a separate device capable of being connected to or separated from the X-ray apparatus 100.

The X-ray apparatus 100 may further include a manipulator 140 for providing a user with an interface for manipulating the X-ray apparatus 100. The manipulator 140 may include an output unit 141 and an input unit 142. The input unit 142 may receive from a user a command for manipulating the X-ray apparatus 100 and various types of information related to X-ray photographing. The controller 150 may control or manipulate the X-ray apparatus 100 according to the information received by the input unit 142. The output unit 141 may output sound representing information related to a photographing operation such as the X-ray radiation under the control of the controller 150.

The workstation 110 and the X-ray apparatus 100 may be connected to each other by wire or wirelessly. When they are connected to each other wirelessly, a device (not shown) for synchronizing clock signals with each other may be further included. The workstation 110 and the X-ray apparatus 100 may exist within physically separate spaces.

The workstation 110 may include an output unit 111, an input unit 112, and a controller 113. The output unit 111 and the input unit 112 provide a user with an interface for manipulating the workstation 110 and the X-ray apparatus 200. The controller 113 may control the workstation 110 and the X-ray apparatus 200.

The X-ray apparatus 100 may be controlled via the workstation 110 or may be controlled by the controller 150 included in the X-ray apparatus 100. Accordingly, a user may control the X-ray apparatus 100 via the workstation 110 or may control the X-ray apparatus 100 via the manipulator 140 and the controller 150 included in the X-ray apparatus 100. In other words, a user may remotely control the X-ray apparatus 100 via the workstation 110 or may directly control the X-ray apparatus 100.

Although the controller 113 of the workstation 110 is separate from the controller 150 of the X-ray apparatus 100 in FIG. 1, FIG. 1 is only an example. In some embodiments, the controllers 113 and 150 may be integrated into a single controller, and the single controller may be included in only one of the workstation 110 and the X-ray apparatus 100. Hereinafter, the controllers 113 and 150 may denote the controller 113 of the workstation 110 and/or the controller 150 of the X-ray apparatus 100.

The output unit 111 and the input unit 112 of the workstation 110 may provide a user with an interface for manipulating the X-ray apparatus 100, and the output unit 141 and the input unit 142 of the X-ray apparatus 100 may also provide a user with an interface for manipulating the X-ray apparatus 100. Although the workstation 110 and the X-ray apparatus 100 include the output units 111 and 141, respectively, and the input units 112 and 142, respectively, in FIG. 1, embodiments are not limited thereto. Only one of the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include a keyboard, a mouse, a touch screen, a voice recognizer, a fingerprint recognizer, an iris recognizer, and other input devices which are well known to one of ordinary skill in the art. The user may input a command for radiating the X-ray via the input units 112 and 142, and the input units 112 and 142 may include a switch for inputting the command. The switch may be configured so that a radiation command for radiating the X-ray may be input only when the switch is pushed in two steps.

In other words, when the user pushes the switch, a prepare command for performing a pre-heating operation for X-ray radiation may be input, and in this state, when the user pushes the switch deeper, a radiation command for performing substantial X-ray radiation may be input. When the user manipulates the switch as described above, the controllers 113 and 150 generate signals corresponding to the commands input through the switch manipulation, that is, a prepare signal, and transmit the generated signals to the high voltage generator 121 generating a high voltage for generating the X-ray.

When the high voltage generator 121 receives the prepare signal from the controllers 113 and 150, the high voltage generator 121 starts a pre-heating operation, and when the pre-heating is finished, the high voltage generator 121 outputs a ready signal to the controllers 113 and 150. In addition, the detector 130 also needs to prepare to detect the X-ray, and thus the high voltage generator 121 performs the pre-heating operation and the controllers 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 outputs a ready signal to the controllers 113 and 150.

When the pre-heating operation of the high voltage generator 121 is finished and the detector 130 is ready to detect the X-ray, the controllers 113 and 150 transmit a radiation signal to the high voltage generator 121, the high voltage generator 121 generates and applies the high voltage to the X-ray source 122, and the X-ray source 122 radiates the X-ray.

When the controllers 113 and 150 transmit the radiation signal to the high voltage generator 121, the controllers 113 and 150 may transmit a sound output signal to the output units 111 and 141 so that the output units 111 and 141 output a predetermined sound and the object may recognize the radiation of the X-ray. The output units 111 and 141 may also output a sound representing information related to photographing in addition to the X-ray radiation. In FIG. 1, the output unit 141 is included in the manipulator 140; however, the embodiments are not limited thereto, and the output unit 141 or a portion of the output unit 141 may be located elsewhere. For example, the output unit 141 may be located on a wall of an examination room in which the X-ray photographing of the object is performed.

The controllers 113 and 150 control locations of the X-ray radiator 120 and the detector 130, photographing timing, and photographing conditions, according to photographing conditions set by the user.

In more detail, the controllers 113 and 150 control the high voltage generator 121 and the detector 130 according to the command input via the input units 112 and 142 so as to control radiation timing of the X-ray, an intensity of the X-ray, and a region radiated by the X-ray. In addition, the controllers 113 and 150 adjust the location of the detector 130 according to a predetermined photographing condition, and controls operation timing of the detector 130.

Furthermore, the controllers 113 and 150 generate a medical image of the object by using image data received via the detector 130. In detail, the controllers 113 and 150 may receive the image data from the detector 130, and then, generate the medical image of the object by removing noise from the image data and adjusting a dynamic range and interleaving of the image data.

The output units 111 and 141 may output the medical image generated by the controllers 113 and 150. The output units 111 and 141 may output information that is necessary for the user to manipulate the X-ray apparatus 100, for example, a user interface (UI), user information, or object information. Examples of the output units 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

The workstation 110 shown in FIG. 1 may further include a communicator (not shown) that may be connected to a server 162, a medical apparatus 164, and a portable terminal 166 via a network 15.

The communicator may be connected to the network 15 by wire or wirelessly to communicate with the server 162, the medical apparatus 164, or the portable terminal 166. The communicator may transmit or receive data related to diagnosis of the object via the network 15, and may also transmit or receive medical images captured by the medical apparatus 164, for example, a CT apparatus, an MRI apparatus, or an X-ray apparatus. Moreover, the communicator may receive a medical history or treatment schedule of an object (e.g., a patient) from the server 162 to diagnose a disease of the object. Also, the communicator may perform data communication with the portable terminal 166 such as a mobile phone, a personal digital assistant (PDA), or a laptop computer of a medical doctor or a client, as well as the server 162 or the medical apparatus 164 in a hospital.

The communicator may include one or more elements enabling communication with external apparatuses. For example, the communicator may include a local area communication module, a wired communication module, and a wireless communication module.

The local area communication module refers to a module for performing local area communication with an apparatus located within a predetermined distance. Examples of local area communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module refers to a module for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include a plurality of digital signal processors (DSPs), an ultra-small calculator, and a processing circuit for special purposes (for example, high speed analog/digital (A/D) conversion, high speed Fourier transformation, and an array process).

In addition, communication between the workstation 110 and the X-ray apparatus 100 may be performed using a high speed digital interface, such as low voltage differential signalling (LVDS), asynchronous serial communication, such as a universal asynchronous receiver transmitter (DART), a low latency network protocol, such as error synchronous serial communication or a controller area network (CAN), or any of other various communication methods that are well known to one of ordinary skill in the art.

FIG. 2 is a perspective view of a fixed type X-ray apparatus 200. The fixed type X-ray apparatus 200 may be another embodiment of the X-ray apparatus 100 of FIG. 1. Components included in the fixed type X-ray apparatus 200 that are the same as those of the X-ray apparatus 100 of FIG. 1 use the same reference numerals, and repeated descriptions thereof will be omitted.

Referring to FIG. 2, the fixed type X-ray apparatus 200 includes a manipulator 140 providing a user with an interface for manipulating the X-ray apparatus 200, an X-ray radiator 120 radiating an X-ray to an object, a detector 130 detecting an X-ray that has passed through the object, first, second, and third motors 211, 212, and 213 providing a driving power to transport the X-ray radiator 120, a guide rail 220, a moving carriage 230, and a post frame 240. The guide rail 220, the moving carriage 230, and the post frame 240 are formed to transport the X-ray radiator 120 by using the driving power of the first, second, and third motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other at 90°.

The first guide rail 221 is provided on the ceiling of an examination room in which the X-ray apparatus 200 is disposed.

The second guide rail 222 is located under the first guide rail 221, and is mounted so as to slide along the first guide rail 221. A roller (not shown) that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90°, and may be parallel to the ceiling of the examination room.

The moving carriage 230 is disposed under the second guide rail 222 so as to move along the second guide rail 222. A roller (not shown) moving along the second guide rail 222 may be provided on the moving carriage 230.

Therefore, the moving carriage 230 may move in the first direction D1 together with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be foldable, and thus, the post frame 240 may have a length that is adjustable in a vertical direction of the examination room while in a state of being fixed to the moving carriage 230.

A third direction D3 is defined as a direction in which the length of the post frame 240 increases or decreases. Therefore, the third direction D3 may be perpendicular to the first direction D1 and the second direction D2.

The detector 130 detects the X-ray that has passed through the object, and may be combined with a table type receptor 290 or a stand type receptor 280.

A rotating joint 250 is disposed between the X-ray radiator 120 and the post frame 240. The rotating joint 250 allows the X-ray radiator 120 to be coupled to the post frame 240, and supports a load applied to the X-ray radiator 120.

The X-ray radiator 120 connected to the rotating joint 250 may rotate on a plane that is perpendicular to the third direction D3. In this case, a rotating direction of the X-ray radiator 120 may be defined as a fourth direction D4.

Also, the X-ray radiator 120 may be configured to be rotatable on a plane perpendicular to the ceiling of the examination room. Therefore, the X-ray radiator 120 may rotate in a fifth direction D5 that is a rotating direction about an axis that is parallel with the first direction D1 or the second direction D2, with respect to the rotating joint 250.

The first, second, and third motors 211, 212, and 213 may be provided to move the X-ray radiator 120 in the first, second, and third directions D1, D2, and D3. The first, second, and third motors 211, 212, and 213 may be electrically driven, and the first, second, and third motors 211, 212, and 213 may respectively include an encoder.

The first, second, and third motors 211, 212, and 213 may be disposed at various locations in consideration of design convenience. For example, the first motor 211, moving the second guide rail 222 in the first direction D1, may be disposed around the first guide rail 221, the second motor 212, moving the moving carriage 230 in the second direction D2, may be disposed around the second guide rail 222, and the third motor 213, increasing or reducing the length of the post frame 240 in the third direction D3, may be disposed in the moving carriage 230. In another example, the first, second, and third motors 211, 212, and 213 may be connected to a driving power transfer unit (not shown) so as to linearly move the X-ray radiator 120 in the first, second, and third directions D1, D2, and D3. The driving power transfer unit may be a combination of a belt and a pulley, a combination of a chain and a sprocket, or a shaft, which are generally used.

In another example, motors (not shown) may be disposed between the rotating joint 250 and the post frame 240 and between the rotating joint 250 and the X-ray radiator 120 in order to rotate the X-ray radiator 120 in the fourth and fifth directions D4 and D5.

The manipulator 140 may be disposed on a side surface of the X-ray radiator 120.

Although FIG. 2 shows the fixed type X-ray apparatus 200 connected to the ceiling of the examination room, the fixed type X-ray apparatus 200 is merely an example for convenience of comprehension. That is, X-ray apparatuses according to embodiments of the present disclosure may include X-ray apparatuses having various structures that are well known to one of ordinary skill in the art, for example, a C-arm-type X-ray apparatus and an angiography X-ray apparatus, in addition to the fixed type X-ray apparatus 200 of FIG. 2.

FIG. 3 is a diagram showing a configuration of a mobile X-ray apparatus 300 capable of performing an X-ray photographing operation regardless of a place where the photographing operation is performed. The mobile X-ray apparatus 300 may be another embodiment of the X-ray apparatus 100 of FIG. 1. Components included in the mobile X-ray apparatus 300 that are the same as those of the X-ray apparatus 100 of FIG. 1 use the same reference numerals as those used in FIG. 1, and a repeated description thereof will be omitted.

Referring to FIG. 3, the mobile X-ray apparatus 300 includes a transport unit 370 including a wheel for transporting the mobile X-ray apparatus 300, a main unit 305, an X-ray radiator 120, and a detector 130 detecting an X-ray that is radiated from the X-ray radiator 120 toward an object and transmitted through the object. The main unit 305 includes a manipulator 140 providing a user with an interface for manipulating the mobile X-ray apparatus 300, a high voltage generator 121 generating a high voltage applied to an X-ray source 122, and a controller 150 controlling overall operations of the mobile X-ray apparatus 300. The X-ray radiator 120 includes the X-ray source 122 generating the X-ray, and a collimator 123 guiding a path along which the generated X-ray is emitted from the X-ray source 122 and adjusting an irradiation region radiated by the X-ray.

The detector 130 in FIG. 3 may not be combined with any receptor, and the detector 130 may be a portable detector which can exist anywhere.

In FIG. 3, the manipulator 140 is included in the main unit 305; however, embodiments are not limited thereto. For example, as illustrated in FIG. 2, the manipulator 140 of the mobile X-ray apparatus 300 may be disposed on a side surface of the X-ray radiator 120.

FIG. 4 is a view illustrating an X-ray detector 400 according to an exemplary embodiment. The X-ray detector 400 illustrated in FIG. 4 may be an embodiment of the detectors 130 illustrated in FIGS. 1 to 3. The X-ray detector 400 illustrated in FIG. 4 may be an indirect type detector.

Referring to FIG. 4, the X-ray detector 400 may include a scintillator (not shown), a photodetecting substrate 410, a bias circuit 430, a gate driver 450, and a read-out circuit 470.

The scintillator receives X-rays radiated from the X-ray source 122 (refer to FIGS. 1 to 3) and converts the X-rays into light.

The photodetecting substrate 410 receives the light from the scintillator and converts the light into an electric signal. The photodetecting substrate 410 may include gate lines GL, data lines DL, TFTs 412, photodiodes 414, and bias lines BL.

The photodiodes 414 are arranged in a matrix shape and connected to the TFTs 412, respectively. The TFTs 412 illustrated in FIG. 4 are examples. That is, other switching devices may be used. In the exemplary embodiment shown in FIG. 4, sixteen photodiodes 414 are arranged in four rows and four columns.

The gate lines GL may be formed in a first direction DR1, and the data lines DL may be formed in a second direction DR2 crossing the first direction DR1. The first direction DR1 and the second direction DR2 may be perpendicular to each other. In each column of the matrix shape extending in the second direction DR2, N data lines DL are formed where N is greater than 1. In FIG. 4, N is 2. However, N may be greater than 2. If N is 2 as shown in FIG. 4, two data lines CIN1 and CIN2 may be formed in each column of data lines DL1, DL2, DL3, and DL4. For example, two data lines DL2(CIN1) and DL2(CIN2) may be formed in the second column. N data lines formed in each column may be referred to as N channel data lines CIN1 and CIN2.

In the exemplary embodiment shown in FIG. 4, four gate lines GL and eight data lines DL are illustrated. The description given with reference to FIG. 4 is based on the case of N=2. However, N may be greater than 2.

The TFTs 412 may be arranged in the matrix shape in the first direction DR1 and the second direction DR2. Each of the TFTs 412 may be electrically connected to one of the gate lines GL. Each TFT 412 included in a column of the matrix shape extending in the second direction DR2 may be connected to one of N data lines CIN1 and CIN2 (N=2 in FIG. 4). In FIG. 4, TFTs 412 connected to a first gate line GL1 and a third gate line GL3 are connected to first channel data lines CIN1, and TFTs 412 connected to a second gate line GL2 and a fourth gate line GL4 are connected to second channel data lines CIN2.

A gate of each TFT 412 may be electrically connected to a gate line GL, and a source of each TFT 412 may be electrically connected to a data line DL. In FIG. 4, sixteen TFTs 412 (in a 4×4 arrangement) are shown as an example.

The photodiodes 414 may be arranged in the matrix shape in the first direction DR1 and the second direction DR2 such that the photodiodes 414 may correspond to the TFTs 412 in a one-to-one relation. Each of the photodiodes 414 may be electrically connected to one of the TFTs 412. An N-side electrode of each of the photodiodes 414 may be electrically connected to a drain of the TFT 412. FIG. 4 shows sixteen photodiodes 414 (in a 4×4 arrangement) as an example.

The bias lines BL are electrically connected to the photodiodes 414. Each of the bias lines BL may be electrically connected to P-side electrodes of an array of photodiodes 414. For example, the bias lines BL may be substantially parallel with the second direction DR2 and may be electrically connected to the photodiodes 414. Alternatively, the bias lines BL may be substantially parallel with the first direction DR1 and may be electrically connected to the photodiodes 414. In the exemplary embodiment shown in FIG. 4, four bias lines BL are formed in the second direction DR2.

The bias circuit 430 is electrically connected to the bias lines BL to apply a driving voltage to the bias lines BL. The bias circuit 430 may selectively apply a reverse bias voltage or a forward bias voltage to the photodiodes 414. A reference voltage may be applied to the N-side electrodes of the photodiodes 414. The reference voltage may be applied through the read-out circuit 470. The bias circuit 430 may apply a voltage lower than the reference voltage to the P-side electrodes of the photodiodes 414 so as to apply a reverse bias voltage to the photodiodes 414. In addition, the bias circuit 430 may apply a voltage higher than the reference voltage to the P-side electrodes of the photodiodes 414 so as to apply a forward bias voltage to the photodiodes 414.

The gate driver 450 is electrically connected to the gate lines GL and thus may apply gate signals to the gate lines GL. For example, when the gate signals are applied to the gate lines GL, the TFTs 412 may be turned on by the gate signals. On the other hand, when the gate signals are not applied to the gate lines GL, the TFTs 412 may be turned off.

The read-out circuit 470 is electrically connected to the data lines DL. If light received on the photodetecting substrate 410 is converted into an electric signal, the electric signal may be read out by the read-out circuit 470 through the data lines DL.

Although not shown in FIG. 4, if the X-ray detector 400 is a wireless detector, the X-ray detector 400 may further include a battery unit and a wireless communication interface.

Hereinafter, exemplary operations of the X-ray detector 400 will be described with reference to FIG. 5. While the X-ray detector 400 is operated, the bias circuit 430 may apply a reverse bias voltage to the photodiodes 414.

FIG. 5 is a view illustrating exemplary waveforms of gate signals applied from the gate driver 450 of the X-ray detector 400 illustrated in FIG. 4.

Referring to FIGS. 4 and 5, gate signals may be applied to the gate lines GL1 to GL4 through the gate driver 450. In FIG. 5, the TFTs 412 are turned on by high-level gate signals and are turned off by low-level gate signals. However, it is apparent that turn-on gate signals and turn-off gate signals may vary according to the type of the TFTs 412.

While the TFTs 412 are turned off, each of the photodiodes 414 may receive light from the scintillator and generate electron-hole pairs to accumulate an electric charge. The amount of electric charge accumulated in each of the photodiodes 414 may correspond to the intensity of received X-rays.

Next, the gate driver 450 applies turn-on gate signals to the gate lines GL to turn on the TFTs 412. Turn-on gate signals may be simultaneously applied to N TFTs 412 (N=2 in FIG. 4) included in a second-direction column and connected to different data lines CIN1 and CIN2. That is, TFTs 412 included in N rows extending in the first direction DR1 may be simultaneously turned on by turn-on gate signals.

Referring to FIGS. 4 and 5, turn-on gate signals are simultaneously applied to the first gate line GL1 and the second gate line GL2, and then turn-on gate signals are simultaneously applied to the third gate line GL3 and the fourth gate line GL4.

If the TFTs 412 are turned on by the turn-on gate signals applied to the gate lines GL, photocurrents may flow to the read-out circuit 470 through the data lines DL by the electric charges accumulated in the photodiodes 414. First, after turn-on gate signals are simultaneously applied to the first gate line GL1 and the second gate line GL2, photocurrents may flow to the read-out circuit 470 from photodiodes 414 connected to the first gate line GL1 and the second gate line GL2. Next, after turn-on gate signals are simultaneously applied to the third gate line GL3 and the fourth gate line GL4, photocurrents may flow to the read-out circuit 470 from photodiodes 414 connected to the third gate line GL3 and the fourth gate line GL4.

The read-out circuit 470 may convert the received photocurrents into image data. The read-out circuit 470 may output the image data to an external device. The image data may be in the form of an analog signal or a digital signal corresponding to the photocurrents. The image data may be constituted by a plurality of pixels arranged in a matrix shape. The resolution of the image data may be defined by the number of the pixels or the size of the matrix shape formed by the pixels. The matrix-type pixels may correspond to the photodiodes 414 arranged in a matrix shape.

FIG. 6 is a view of an X-ray detector 40 provided not in accordance with the exemplary embodiment, and FIG. 7 is a view illustrating exemplary waveforms of gate signals applied from a gate driver 45 of the X-ray detector 40 illustrated in FIG. 6.

Unlike in the X-ray detector 400 illustrated in FIG. 4, one data line DL is formed in each column of the X-ray detector 40 of FIG. 6 extending in a second direction DR2. In FIG. 6, four gate lines GL and four data lines DL are illustrated.

Referring to FIGS. 6 and 7, the gate driver 45 sequentially applies turn-on signals to the gate lines GL along the second direction DR2. That is, turn-on signals are sequentially applied to first to fourth gate lines GL1 to GL4.

If FIGS. 5 and 7 are compared, it takes a time period of t in FIG. 5 to turn on the third gate line GL3 after turning on the first gate line GL1, but it takes a time period of about 2t in FIG. 7. In the case of FIG. 7, it takes about double the time to apply turn-on signals to all the gate lines GL1 to GL4 of the X-ray detector 40 compared to the case of FIG. 5. Therefore, the X-ray detection speed of the X-ray detector 40 illustrated in FIGS. 6 and 7 is about ½ the X-ray detection speed of the X-ray detector 400 of the exemplary embodiment illustrated in FIGS. 4 and 5. That is, the X-ray detector 400 of the exemplary embodiment may have improved X-ray detection speed.

The X-ray detector 400 of the exemplary embodiment will now be described in more detail with reference to FIGS. 8 to 10.

FIG. 8 is a view illustrating a read-out circuit 500 included in the X-ray detector 400 of the exemplary embodiment.

The read-out circuit 500 illustrated in FIG. 8 may be an embodiment of the read-out circuit 470 illustrated in FIG. 4. The read-out circuit 500 illustrated in FIG. 8 is provided for the case in which the X-ray detector 400 of FIG. 4 includes two channel data lines CIN1 and CIN2.

Referring to FIGS. 4 and 8, the read-out circuit 500 may include a plurality of holder units 510-1, . . . , 501-4 and a multiplexer 520.

Each of the plurality of sample holder units 510-1, . . . , 510-4 is connected to two channel data lines CIN1 and CIN2 of each column shown in FIG. 4. For example, a fourth sample holder unit 510-4 may be connected to two channel data lines DL4(CIN1) and DL4(CIN2) of a fourth column of FIG. 4 through pads. In FIG. 8, four sample holder units 510-1, . . . , 510-4 are illustrated. The number of the sample holder units may be equal to the number of the columns of the matrix shape of the X-ray detector 400.

Each of the sample holder units 510-1, . . . , 510-4 may include: a first input stage 511 and a first sample holder 513 that are connected to a first channel data line CIN1; and a second input stage 512 and a second sample holder 514 that are connected to a second channel data line CIN2.

The multiplexer 520 is connected to the sample holder units 510-1, . . . 510-4.

As described above, photocurrents may flow from photodiodes 414 connected to turned-on switching devices to the read-out circuit 500 through data lines DL1(CIN1), . . . , DL4(CIN4) connected to the turned-on switching devices.

The two sample holders 513 and 514 included in each of the sample holder units 510-1, . . . , 510-4 may accumulates sample electric charges based on the photocurrents. The multiplexer 520 may sequentially output the sample electric charges accumulated in the sample holders 513 and 514 through an output pad VD. X-ray image data may be obtained based on output signals transmitted through the output pad VD. The read-out circuit 500 may further include an image processor (not shown) to obtain image data based on output signals.

FIG. 8 illustrates the case in which N is 2, that is, two channel data lines CIN1 and CIN2 are formed in each column. However, N may be greater than 2. That is, each of the sample holder units 510-1, . . . , 510-4 may include N input stages and N sample holders that are respectively connected to N channel data lines.

FIG. 9 is a view illustrating examples of the sample holder unit 510-1 and the multiplexer 520 of the read-out circuit 500 illustrated in FIG. 8. In FIG. 9, only the sample holder unit 510-1 of the sample holder units 510-1, . . . , 510-4 is illustrated. However, the other sample holder units 510-2, . . . , 510-4 may have the same structure as the sample holder unit 510-1.

Referring to FIG. 9, a first channel data line DL1(CIN1) is connected to a first input stage 511-1 and a first sample holder 513-1. A second channel data line DL1(CIN2) is connected to a second input stage 512-1 and a second sample holder 514-1. The read-out circuit 500 may further include low pass filters (LPFs) between the input stages 511-1 and 512-1 and the sample holders 513-1 and 514-1.

Each of the input stages 511-1 and 512-1 may include an input capacitor Cin and an amplifier AMP connected to the input capacitor Cin. A switch device controllable by a reset signal RST may be connected to both ends of the input capacitor Cin.

Each of the sample holders 513-1 and 514-1 may include a first capacitor C1 and a second capacitor C2.

Ends of the first capacitors C1 may be respectively connected to the input stages 511-1 and 512-1 through switching devices controllable by first sample signals SH1. A reference voltage may be applied to the other ends of the first capacitors C1.

Ends of the second capacitors C2 may be respectively connected to the input stages 511-1 and 512-1 through switching devices controllable by second sample signals SH2. The reference voltage may be applied to the other ends of the second capacitors C2.

In detail, the switching device connected to the first capacitor C1 of the first sample holder 513-1 may be controlled by a first sample signal SH1(CIN1) of a first channel, and the switching device connected to the second capacitor C2 of the first sample holder 513-1 may be controlled by a second sample signal SH2(CIN1) of the first channel.

The switching device connected to the first capacitor C1 of the second sample holder 514-1 may be controlled by a first sample signal SH1(CIN2) of a second channel, and the switching device connected to the second capacitor C2 of the second sample holder 514-1 may be controlled by a second sample signal SH2(CIN2) of the second channel.

The multiplexer 520 may include: first buffers BF1 521-1 and 521-2 respectively connected to the first capacitors C1; and second buffers BF2 522-1 and 522-2 respectively connected to the second capacitors C2. In addition, the multiplexer 520 may further include: a first output buffer B01 connected to the first buffers BF1 521-1 and 521-2; and a second output buffer B02 connected to the second buffers BF2 522-1 and 522-2. An output signal of the first output buffer B01 may be output through a first output pad VD1, and an output signal of the second output buffer B02 may be output through a second output pad VD2.

The first buffers BF1 521-1 and 521-2 may be connected to the first output buffer B01 through switching devices. In addition, the second buffers BF2 522-1 and 522-2 may be connected to the second output buffer B02 through switching devices.

The switching devices connected to the first and second buffers 521-1 and 522-1 that are connected to the first sample holder 513-1 connected to the first channel data line DL1(CIN1) may be controlled by first scan signals SCAN1.

The switching devices connected to the first and second buffers 521-2 and 522-2 that are connected to the second sample holder 514-2 connected to the second channel data line DL1(CIN2) may be controlled by second scan signals SCAN2.

Although not shown, switching devices controllable by third scan signals SCAN3 may be connected between sample holders connected to the next data line DL2(CIN1) (refer to FIG. 4) and the first and second output buffers B01 and B02. Similarly, switching devices controllable by eighth scan signals SCAN8 may be connected between sample holders connected to the last data line DL4(CIN2) (refer to FIG. 4) and the first and second output buffers B01 and B02.

The first to eighth scan signals SCAN1 to SCAN 8 may be sequentially applied to turn on the switching devices.

Therefore, if the switching devices are turned on or off by the first scan signals SCAN1, a first sample electric charge accumulated in the first capacitor C1 of the first sample holder 513-1 may be output through the first output pad VD1, and a second sample electric charge accumulated in the second capacitor C2 of the first sample holder 513-1 may be output through the second output pad VD2. At this time, the first and second sample electric charges may be simultaneously output. Next, if the switching devices are turned on by the second scan signals SCAN2, a first sample electric charge accumulated in the first capacitor C1 of the second sample holder 514-1 may be output through the first output pad VD1, and a second sample electric charge accumulated in the second capacitor C2 of the second sample holder 514-1 may be output through the second output pad VD2. In this manner, first and second sample charges accumulated in the sample holders may be sequentially output.

FIG. 10 is a view illustrating exemplary waveforms of signals applied to elements of the X-ray detector 400 explained with reference to FIGS. 4 and 9. With reference to FIGS. 4, 9, and 10, an explanation will now be given of how the X-ray detector 400 is operated according to time.

If the level of a reset signal RST becomes high, the input capacitors of the input stages 511-1 and 512-1 are short-circuited. Therefore, a voltage difference between both ends of each of the input capacitors Cin becomes zero. That is, the voltage difference between both ends of each of the input capacitors Cin may be initialized by the reset signal RST.

After the input capacitors Cin are initialized, the level of a shift register clear signal SR_CLR may become high to reset the operation of the multiplexer 520. If the level of the shift register clear signal SR_CLR becomes high, the reset signal RST returns to low level.

Next, the level of a first sample signal SH1(CIN1) of a first channel and the level of a first sample signal SH1(CIN2) of a second channel become high level at the same time. Then, the input capacitors Cin of the input stages 511-1 and 512-1 are electrically connected to the first capacitors C1 of the sample holders 513-1 and 514-1, respectively. The first capacitors C1 accumulate first sample electric charges based on electric charges accumulated in the input capacitors Cin electrically connected thereto. The first sample electric charges may become noise voltages if all the TFTs 412 (refer to FIG. 4) of the X-ray detector 400 (refer to FIG. 4) are turned off.

Next, turn-on gate signals are simultaneously applied to the first gate line GL1 and the second gate line GL2. The input stages 511-1 and 512-1 are electrically connected to photodiodes 414, and the input capacitors Cin accumulate photocharges based on photocurrents from the photodiodes 414.

Next, the level of a second sample signal SH2(CIN1) of the first channel and the level of a second sample signal SH2(CIN2) of the second channel become high level at the same time. Then, the input capacitors Cin of the input stages 511-1 and 512-1 are electrically connected to the second capacitors C2 of the sample holders 513-1 and 514-1, respectively. The second capacitors C2 accumulate second sample electric charges based on the photocharges accumulated in the input capacitors Cin electrically connected thereto.

Next, the multiplexer 520 may sequentially output the sample electric charges accumulated in the sample holders 513-1 and 514-1 through the output pads VD1 and VD2. At this time, the first sample electrode charges of the sample holders 513-1 and 514-1 may be sequentially output through the first output pad VD1, and the second sample electric charges of the sample holders 513-1 and 514-1 may be sequentially output through the second output pad VD2. The first sample electric charges and the second sample electric charges of the sample holders 513-1 and 514-1 may be simultaneously output through the two output pads VD1 and VD2 of the multiplexer 520.

While the sample electric charges accumulated in the sample holders 513-1 and 514-1 are output through the multiplexer 520, the reset signal RST goes back to high level. Therefore, the input capacitors Cin of the input stages 511-1 and 512-1 are short-circuited, and thus the voltage difference between both ends of each of the input capacitors Cin may become zero.

Next, the above-described signal waveforms are repeated. However, turn-on gate signals may be applied to the third gate line GL3 and the fourth gate line GL4.

As described above, exemplary embodiments of the present disclosure may provide an X-detector and an X-ray apparatus that are capable of improving X-ray detection speed. That is, according to the exemplary embodiments, a frame rate for reading out photocurrents of all the photodiodes of the X-ray detector may be decreased, and thus the speed of X-ray detection may be improved. At this time, although the frame rate is decreased, the matrix arrangement of the photodiodes, that is, the resolution of X-ray image data may not be decreased.

In addition, other exemplary embodiments can also be implemented through computer readable code/instructions in/on a medium, e.g., a computer readable medium, to control at least one processing element to implement any above described exemplary embodiment. The medium can correspond to any medium/media permitting the storage and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bit stream according to one or more exemplary embodiments. The media may also be a distributed network, so that the computer readable code may be stored/transferred and executed in a distributed fashion. Furthermore, the processing element could include a processor or a computer processor, and processing elements may be distributed and/or included in a single device.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

The invention claimed is:

1. An X-ray detector comprising:
a plurality of photodiodes arranged in a matrix shape and respectively connected to switching devices;
a plurality of gate lines formed in a first direction and connected to the switching devices;
a plurality of data lines, wherein N data lines are formed in each second-direction column of the matrix shape, wherein N is greater than 1;
a gate driver connected to the plurality of gate lines and configured to apply gate signals for turning on the photodiodes via the switching devices, wherein the gate signals are simultaneously applied to N of the photodiodes that are (i) included in one of the second-direction columns and (ii) connected to different of the N data lines formed in the one second-direction column; and
a read-out circuit connected to the plurality of data lines and configured to read out photocurrents from the plurality of photodiodes and convert the photocurrents into X-ray image data,
wherein each of the switching devices included in each second-direction column of the matrix shape is connected to one of the N data lines.

2. The X-ray detector of claim 1, wherein:
the gate lines are formed in rows in the first direction of the matrix shape, and
the gate driver is configured to simultaneously apply the gate signals to N of the gate lines.

3. The X-ray detector of claim 1, wherein switching devices included in N rows formed in the first direction in the matrix shape are simultaneously turned on by the gate signals.

4. The X-ray detector of claim 3, wherein photocurrents from photodiodes connected to the turned-on switching devices are input to the read-out circuit through the data lines connected to the turned-on switching devices.

5. The X-ray detector of claim 4, wherein the read-out circuit comprises:
N sample holders connected to the N data lines formed in each second-direction column of the matrix shape; and
a multiplexer connected to the N sample holders.

6. The X-ray detector of claim 5, wherein the N sample holders are configured to accumulate sample electric charges based on photocurrents from photodiodes that are electrically respectively connected to the N sample holders, and
the multiplexer is configured to sequentially output the sample electric charges accumulated in the N sample holders.

7. The X-ray detector of claim 5, wherein the read-out circuit further comprises input stages between the data lines and the N sample holders,
wherein the input stages comprise input capacitors configured to accumulate photocharges based on the photocurrents.

8. The X-ray detector of claim 7, wherein each of the N sample holders comprises a first capacitor and a second capacitor,
wherein, before the switching devices included in the N rows are simultaneously turned on by the gate signals, the first capacitors are electrically connected to the input capacitors and accumulate first sample electric charges, and
after the switching devices included in the N rows are simultaneously turned on by the gate signals, the second capacitors are electrically connected to the input capacitors and accumulate second sample electric charges based on the photocharges.

9. The X-ray detector of claim 8, wherein the multiplexer is configured to simultaneously output the first and second sample electric charges.

10. The X-ray detector of claim 9, wherein the read-out circuit is configured to obtain the X-ray image data based on a difference between the first and second sample electric charges.

11. An X-ray apparatus comprising:
an X-ray radiator configured to radiate X-rays; and
a detector configured to detecting the radiated X-rays, wherein the detector comprises:
a scintillator configured to convert the X-rays into light;
a plurality of photodiodes arranged in a matrix shape and respectively connected to switching devices;
a plurality of gate lines formed in a first direction and connected to the switching devices;
a plurality of data lines, wherein N data lines are formed in each second-direction column of the matrix shape, wherein N is greater than 1;
a gate driver connected to the plurality of gate lines and configured to apply gate signals for turning on the photodiodes via the switching devices, wherein the gate signals are simultaneously applied to N of the photodiodes that are (i) included in one of the second-direction columns and (ii) connected to different of the N data lines formed in the one second-direction column; and
a read-out circuit connected to the plurality of data lines and configured to read out photocurrents from the plurality of photodiodes and convert the photocurrents into X-ray image data,
wherein each of switching devices included in each second-direction column of the matrix shape is connected to one of the N data lines.

12. The X-ray apparatus of claim 11, wherein:
the gate lines are formed in rows in the first direction of the matrix shape, and
the gate driver is configured to simultaneously apply the gate signals to N of the gate lines.

13. The X-ray apparatus of claim 11, wherein switching devices included in N rows formed in the first direction in the matrix shape are configure to simultaneously turn on by the gate signals.

14. The X-ray apparatus of claim 13, wherein photocurrents from photodiodes connected to the turned-on switching devices are input to the read-out circuit through the data lines connected to the turned-on switching devices.

15. The X-ray apparatus of claim 14, wherein the read-out circuit comprises:
N sample holders connected to the N data lines formed in each second-direction column of the matrix shape; and
a multiplexer connected to the N sample holders.

16. The X-ray apparatus of claim 15, wherein the N sample holders are configured to accumulate electric signals based on photocurrents from photodiodes that are respectively electrically connected to the N sample holders, and
the multiplexer sequentially are configured to output the electric signals accumulated in the N sample holders.

17. The X-ray apparatus of claim 15, wherein the read-out circuit further comprises input stages between the data lines and the N sample holders,
wherein the input stages comprise input capacitors configured to accumulate photocharges based on the photocurrents.

18. The X-ray apparatus of claim 17, wherein each of the N sample holders comprises a first capacitor and a second capacitor,
wherein, before the switching devices included in the N rows are simultaneously turned on by the gate signals, the first capacitors are electrically connected to the input capacitors and accumulate first sample electric charges, and
after the switching devices included in the N rows are simultaneously turned on by the gate signals, the second capacitors are electrically connected to the input capacitors and accumulate second sample electric charge.

19. The X-ray apparatus of claim 18, wherein the multiplexer is configured to simultaneously output the first and second sample electric charges.

20. The X-ray apparatus of claim 19, wherein the read-out circuit is configured to obtain the X-ray image data based on a difference between the first and second sample electric charges.

* * * * *